US005427792A

United States Patent [19]
Zrein et al.

[11] Patent Number: 5,427,792
[45] Date of Patent: Jun. 27, 1995

[54] PEPTIDES, ANALOGUES AND MIXTURES THEREOF FOR DETECTING AND ELICITING ANTIBODIES TO THE E1 AND E2 PROTEIN OF RUBELLA VIRUS

[75] Inventors: Maan Zrein, Laval; Martial Lacroix, Brossard, both of Canada

[73] Assignee: BioChem Immunosystems, Inc., Montreal, Canada

[21] Appl. No.: 927,071

[22] Filed: Aug. 7, 1992

Related U.S. Application Data

[63] Continuation-in-part of Ser. No. 397,767, Aug. 23, 1989, Pat. No. 5,164,481.

[51] Int. Cl.[6] .................. A61K 39/20; C12N 15/40; C07K 7/06; C07K 7/08

[52] U.S. Cl. .................. 424/219.1; 424/184.1; 424/186.1; 424/218.1; 424/193.1; 424/202.1; 435/7.1; 435/69.3; 530/300; 530/324; 530/325; 530/326; 530/327; 530/328; 530/329; 530/826

[58] Field of Search .................. 530/300, 324–329, 530/826; 424/89, 184.1, 186.1, 218.1, 193.1, 202.1, 219.1; 435/69.3, 7.1

[56] References Cited

FOREIGN PATENT DOCUMENTS

| | | |
|---|---|---|
| 230883 | 7/1983 | Czechoslovakia . |
| 299673 | 4/1989 | European Pat. Off. . |
| WO87/03206 | 2/1987 | WIPO . |

OTHER PUBLICATIONS

P. Argos, "A Possible Homology Between Immunodeficiency Virus p24 Core Protein And Picornaviral VP2 Coat Protein: Prediction Of HIV p24 Antigenic Sites", *EMBO Journal,* 8(3), pp. 779–785 (1989) (Argos).

S. Avrameas, "Coupling Of Enzymes To Proteins With Glutaraldehyde", *Immunochemistry,* 6, pp. 43–52 (1969) (Avarameas).

A. Chagnon and P. Laflamme, "Effect Of Acidity On Rubella Virus", *Canadian Journal of Microbiology,* 10, pp. 501–503 (1964) (Chagnon).

H. H. Chaye et al., "Cellular And Humoral Immune Responses To Rubella Virus Structural Proteins E1, E2, And C", *Jour. Clin. Microbiol.,* 30(9), pp. 2323–2329 (Sep., 1992) (Chave).

D. M. Clarke et al., "Nucleotide Sequence And In Vitro Expression Of Rubella Virus 24S Subgenomic Messenger RNA Encoding The Structural Proteins $E_1$, $E_2$ and C", *Nucleic Acids Research,* 15(7), pp. 3041–3057 (1987) (Clarke).

D. K. Ford et al., "Sequential Follow Up Observations Of A Patient With Rubella Associated Persistent Arthritis", *Annals Rheumatic Discases,* 51, pp. 407–410 (1992) (Ford).

T. K. Frey et al., "Molecular Cloning And Sequencing Of The Region Of The Rubella Virus Genome Coding For Glycoprotein E1", *Virology,* 154, pp. 228–232 (1986) (Frey).

K. Herrmann, "Rubella Virus", *Diagnostic Procedures For Viral, Rickettsial And Clamydial Infections,* Lennette and Schmidt (eds.) 5th Edition, American Public Health Association Inc., Washington, pp. 725–766 (1979) (Herrmann).

L. Ho–Terry et al., "Analysis Of Rubella Virus Complement–Fixing Antigens By Polyacrylamide Gel Electrophoresis", *Archives of Virology,* 87, pp. 219–228 (1986) (Ho–Terry–1).

L. Ho–Terry et al., "Immunological Characterisation Of The Rubella E1 Glycoprotein", *Archives of Virology,* 90, pp. 145–152 (1986) (Ho–Terry–2).

(List continued on next page.)

*Primary Examiner*—Christine M. Nucker
*Assistant Examiner*—Michael Tuscan
*Attorney, Agent, or Firm*—Nixon & Vanderhye

[57] ABSTRACT

This invention discloses linear and cyclic peptides of the E1 and E2 glycoproteins of the rubella virus. These peptides and analogues, mixtures and combinations of them are useful in detecting and quantifying antibodies raised against the rubella virus. They are also useful in raising antibodies to the rubella virus for use in the diagnosis of and protection against rubella viral infections.

14 Claims, 2 Drawing Sheets

OTHER PUBLICATIONS

S. H. Lee et al., "Resurgence Of Congenital Rubella Syndrome In The 1990's", *Jour. Am. Medical Assn.*, 267(19), pp. 2616–2620 (1992) (Lee).

R. Maiolini et al., "A Sandwich Method Of Enzyme-Immunoassay. II. Quantification Of Rheumatoid Factor", *Journal of Immunological Methods*, 20, pp. 25–34 (1978) (Maiolini).

L. A. Mitchell et al., "Characterization Of Rubella Virus-Specific Antibody Responses By Using A New Synthetic Peptide-Based Enzyme-Linked Immunosorbent Assay", *Jour. Clinical Microbiol.*, 30(7), pp. 1841–1847 (1992) (Mitchell).

S. V. Nates et al., "Comparison Of Immune Response To Rubella Virus Proteins In Early And Late Natural Infections", *Microbiologica*, 12, pp. 335–338 (1989) (Nates).

D. Ou et al., "Analysis Of T- And B-Cell Epitopes Of Capsid Protein Of Rubella Virus By Using Synthetic Peptides", *Jour. Virology*, 66(3), pp. 1674–1681 (1992) (Ou).

P. D. Parkman et al., "Attenuated Rubella Virus", *The New England Journal of Medicine*, 275(11), pp. 569–574 (1966) (Parkman).

J. W. Partridge et al., "Congenital Rubella Affecting An Infant Whose Mother Had Rubella Antibodies Before Conception", *British Medical Journal*, 282, pp. 187–188 (1981) (Partridge).

L. Pedneault et al., "Comparision Of A Novel Synthetic Peptide-Based EIA (DETECT-Rubella) With Enzygnost And IMX For The Detection Of Rubella IgG Antibodies", *Abstracts Ann. Meeting Am. Society Microbiol.* (May 26–30, 1992) (Pedneault).

L. E. Schaefer et al., "Evaluation Of Microparticle Enzyme Immunoassays For Immunoglobulins G And M To Rubella Virus And *Toxoplasma-gondii* On The Abbott IMX Automated Analyzer", 27(11), pp. 2410–2413 (1989) (Schaefer).

C. Stahli et al., "High Frequencies Of Antigen-Specific Hybridomas: Dependence On Immunization Parameters And Prediction By Spleen Cell Analysis", *Journal of Immunological Methods*, 32, pp. 297–304 (1980) (Stahli).

R. S. Steece et al., "Comparison Of Enzyme-Linked Immunosorbent Assay, Hemagglutination Inhibition, And Passive Latex Agglutination For Determination Of Rubella Immune Status", *Journal of Clinical Microbiology*, 21(1), pp. 140–142 (1985) (Steece).

Takkinen et al., "Nucleotide Sequence Of The Rubella Virus Capsid Protein Gene Reveals An Unusually High G/C Content", *Journal of General Virology*, 69, pp. 603–612 (1988).

G. M. Terry et al., "Localization Of The Rubella E1 Epitopes", *Archives of Virology*, 98, pp. 189–197 (1988) (Terry-1).

G. M. Terry et al., "A Bio-Engineered Rubella E1 Antigen", *Archives of Virology*, 104, pp. 63–75 (1989) (Terry-2).

M. Trudel et al., "Identification Of Rubella Virus Structural Proteins By Immunoprecipitation", *Journal of Virological Methods*, 5, pp. 191–197 (1982) (Trudel).

A. Voller and D. E. Bidwell, "A Simple Method For Detecting Antibodies To Rubella", *British Journal of Experimental Pathology*, 56, pp. 338–339 (1975) (Voller).

Z. Wang and S. IIan, "Tryptic Peptide Map Analysis Of Structural Polypeptides Of Different Rubella Virus Strains", *Shandong Yike Daxue Xuebao*, 24(3), pp. 6–10 (abstract p. 15) (1986) (Wang).

J. S. Wolinsky et al., "Monoclonal Antibody-Defined Epitope Map Of Expressed Rubella Virus Protein Domains", *Jour. Virology*, 65(8), pp. 3986–3994 (1991) (Wolinsky).

Fig. 1

AMINO ACID SEQUENCE OF THE RUBELLA E1 GLYCOPROTEIN (Therien strain; Accession # A29822; A26884)

```
  1 EEAFTYLCTA PGCATQAPVP VRLAGVRFES KIVDGGCFAP WDLEATGACI  50
                                    ?
 51 CEIPTDVSCE GLGAWVPAAP CARIWNGTQR ACTFWAVNAY SSGGYAQLAS 100

101 YFNPGGSYYK QYHPTACEVE PAFGHSDAAC WGFPTDTVMS VFALASYVQH 150
                                    ?
151 PHKTVRVKFH TETRTVWQLS VAGVSCNVTT EHPFCNTPHG QLEVQVPPDP 200
            ?
201 GDLVEYIMNY TGNQQSRWGL GSPNCHGPDW ASPVCQRHSP DCSRLVGATP 250
         BCH-178 --------------------------------       EP2
         BCH-178cyclic -----------------------------
                                 └──────┘

251 ERPRLRLVDA DDPLLRTAPG PGEVWVTPVI GSQARKCGLH IRAGPYGHAT 300
         EP3                   EP1

301 VEMPEWIHAH TTSDPWHPPG PLGLKFKTVR PVALPRTLAP PRNVRVTGCY 350

351 QCGTPALVEG LAPGGGNCHL TVNGEDVGAV PPGKFVTAAL LNTPPPYQVS 400

401 CGGESDRASA RVIDPAAQSF TGVVYGTHTT AVSETRQTWA EWAAAHWWQL 450

451 TLGATCALPL AGLLACCAKC LYYLRGAIAP R.                   481
```

Fig. 2

AMINO ACID SEQUENCE OF THE E2 RUBELLA GLYCOPROTEIN

```
  1 AGLQPRADMA APPTLPQPPR AHGQHYGHHH HQLPFLGHDG HHGGTLRVGQ  50
Therien    BCH-463 ---------------------- (Gnwvr4, A29822)
TherienBCH-481     ---------------------- (Gnwvr4, A29822)
RA27/3 BCH-933 ---MP---------------------- (Pols_Rubvm, P08563)
Therien         ---------C---------------- (Pols_Rubvt, P07566)

?                    ?
 51 HYRNASDVLP GHWLQGGWGC YNLSDWHQGT HVCHTKHMDF WCVEHARPPP 100

?                    ?
101 ATPTPLTTAA NSTTAATPAT APAPCHAGLN DSCGGFLSGC GPMRLRHGAD 150

151 TRCGRLICGL STTAQYPPTR FGCAMRWGLP PWELVVLTAR PEDGWTCRGV 200

201 PAHPGARCPE LVSPMGRATC SPASALWLAT ANALSLDHAL AAFVLSVPWV 250

251 LIFMVCRRAC RRR.
                                                         263
```

PEPTIDES, ANALOGUES AND MIXTURES THEREOF FOR DETECTING AND ELICITING ANTIBODIES TO THE E1 AND E2 PROTEIN OF RUBELLA VIRUS

This application is a continuation-in-part of Ser. No. 07/397,767, filed Aug. 23, 1989, now U.S. Pat. No. 5,164,481.

TECHNICAL FIELD OF THE INVENTION

This invention relates to novel linear and cyclic peptides and mixtures and combinations thereof useful for detecting and quantifying rubella infections and for eliciting antibodies specific to the rubella virus. These peptides are also useful in the manufacture of vaccines against rubella viral infections. The peptides described in this invention may be useful for distinguishing between various types of immune status to rubella. At least one of the described peptides has the ability to recognize specifically rubella neutralizing antibodies.

BACKGROUND OF THE INVENTION

Rubella was first described in Germany in the 18th century and is, therefore, often referred to as German measles. It is a highly contagious disease characterized by a general rash and a mild fever. Its clinical aspects were, for a long time, confused with other infections, including measles. The major risk associated with rubella infection occurs during the first trimester of pregnancy when severe damage to the fetus can result in deafness, cataracts, cardiac abnormalities and microencephaly.

The rubella virus, the etiologic agent of rubella, belongs to the Togaviridae family. It is a roughly spherical enveloped virus about 60 nm in diameter. Its genome consists of a single positive stranded RNA (10 Kb). The structural polyprotein encoded by this genome consists of two envelope glycoproteins—E1 (58K) and E2(42-47K)—and a nucleocapsid protein—C(33K)—. The viral envelope includes components from the host infected cell membrane, and the two viral glycoproteins E1 and E2. These envelope glycoproteins are responsible for the hemagglutination activity of the rubella virus. E1 and E2 glycoproteins are linked by disulfide bonds to form homo- and heterodimers.

Three strains of rubella virus (Therien, Judith, M33) have been described and portions of their genomes have been sequenced (Frey et al., 1986, Virology 154, 228-232; Terry et al., 1988, Arch. Virol. 98, 189-197; Clarke et al., 1987, Nucl. Acids Res. 15, 3041-3057; Takkinen et al., 1988, J. Gen. Virol. 69, 603-612). The sequences of rubella vaccine strain (RA 27/3) is also known (Nakhasi et al., 1989, Nucl. Acids Res. 17 (11), 4393-4394).

Although rubella can be diagnosed by inoculating infected materials (usually nasopharyngeal secretions) into susceptible cell cultures, the most widely used diagnostic tests are based on the hemagglutinating properties of its glycoproteins. In those assays ("HAI"), the presence in a serum sample of antibodies to the hemagglutinin prevents the virus from binding to red blood cells (usually from chicken blood) thus inhibiting hemagglutination (Peetermans and Huygelen, 1967, Presse Med. 75, 2177-2178 and Lennette and Schmidt, 1979, in "*Diagnostic procedures for viral, rickettsial and chlamydial infections*", 5th Ed. American Public Health Association Inc., Washington). In such assays an increase in HAI antibody titers is an indication of a recent infection.

Since the introduction of enzyme-labeled antibodies (Avrameas, 1969, Immunochemistry 6, 43-52), enzyme immunoassay (EIA) or enzyme-linked-immunosorbent assays (ELISA) have been used for the diagnosis of a large variety of viral and bacterial infections, including rubella infections. Serodiagnosis of rubella infections using ELISA techniques was first described by Voller and Bidwell (1975, Br. J. Exp. Pathol. 56, 338-339).

In ELISA in particular, viral extracts or lysates are typically coated onto the surface of plastic wells so that antibodies (if present) in a serum sample or analyte will bind to the adsorbed proteins from the viral extracts. After appropriate washing, the presence of antibodies bound to the proteins in the well is detected using antibodies to human immunoglobulins conjugated to an enzyme, such as horseradish peroxidase. The level of enzymatic activity is measured in each well after washing off the unbound enzyme. Other forms and variations of the ELISA test are also well known and often used by persons skilled in the art.

The introduction of ELISA for the specific determination of rubella IgM and IgG has been responsible for the rapid decline (i.e., from 45% in 1978-1980 to 19% in 1982) of HAI diagnostic assays for rubella viral infections (Steece et al., 1985, J. Clin. Microbiol. 21 (1), 140-142). Compared to HAI tests, ELISA requires no sera pre treatment and only one or two dilutions per serum sample. The amount of antigenic material used in ELISA is also smaller than what was required in the former HAI assays.

There are several problems with the presently used ELISA diagnostic tests for rubella infection. Variations between different preparations of rubella antigens used to coat the wells are often observed. These variations are likely a consequence of various difficulties encountered in reproducibly isolating the rubella virus. In tissue culture, the virus grows to low titers, is difficult to separate from cellular membrane debris, and is highly labile (Ho-Terry et al., 1986, Arch. Virol. 87, 219-228; Chagnon and LaFlamme, 1964, Can. J. Microbiol. 10, 501-503). This makes it difficult to isolate the virus from cellular debris originating from host cells. In an attempt to overcome this problem, some ELISA techniques for detecting rubella infection use a series of wells coated with extracts prepared with uninfected cells (reference antigens) and a second series of wells coated with extracts prepared from rubella-infected cells (viral antigens). Each serum sample is then tested on both series of wells and the net response is calculated by subtraction of the signal measured on the reference antigens' wells from the one measured on the viral antigens' wells.

Terry et al. (1988, Arch. Virol. 98, 189-197) and Ho-Terry et al. (1986, Arch. Virol. 90, 145-152 and European Patent Application No. 88306191.3) refer to the reactivity of three non-competing monoclonal antibodies directed against the rubella E1 glycoprotein. The epitopes bound by each of these monoclonal antibodies have been identified and designated EP1, EP2 and EP3. Monoclonal antibodies directed to EP1 and EP2 exhibit both hemagglutination inhibition and neutralizing activity. Monoclonal antibodies to EP3 exhibit only neutralizing activity. Synthetic peptides corresponding to the EP1, EP2 or EP3 epitopes have not been reported to date. The location of these three epitopes in the viral genome has been described in Terry et al. (supra).

Lozzi et al. (1990, Arch. Virol. 110, 271–276) have synthesized overlapping octapeptides covering the region between amino acids 243–286 which includes the EP1, EP2, and EP3 epitopes of the E1 glycoprotein. Their goal was to establish the minimal size of each of these epitopes. They tested each octapeptide with a pool of human high titer anti-rubella IgG isolated from subjects hyperimmunized with rubella vaccine (the authors stressed that this pool contained no less that 400 International Units of anti-rubella immunoglobulins/mL and that the HA titer was about 2000 Units/mL). Using this very concentrated anti-rubella preparation, they have detected low reactivity with all of their peptides. Using rubella positive sera from vaccinated and naturally infected patients, they report that they observed a higher background absorbance than when purified and concentrated immunoglobulins were used. This study illustrates the difficulty one faces when trying to identify synthetic peptide antigens of significant use in the design of a diagnostic test or a better vaccine.

More recently, Wolinsky et al. (1991, J. Virol. 65, 3986–3994) have characterized a series of murine monoclonal antibodies reacting with various regions of the E1 and E2 proteins. Using various plasmid constructs, the authors have localized the binding sites of their monoclonal antibodies. Most of the anti-E1 reactivity was located between residue 202 and 283. On E2, the monoclonal antibodies were binding to a relatively large region covering 116 residues at the amino terminus.

The rubella pandemic of 1963–1965 prompted the development of a vaccine against rubella (Parkman et al., 1966, N. Engl. J. Med. 275, 569–574). It is comprised of live attenuated viruses and is immunogenic in at least 95% of the recipients. Neutralizing antibodies generated by the attenuated vaccine appear later than those following a natural infection and at levels as much as ten-fold lower. Vaccine-induced antibodies, nonetheless, effectively protect recipients from the disease. The present rubella vaccines, however, have some drawbacks. For example, a significant proportion of people vaccinated suffer occasional arthritis (mainly seen in adult women), mild rash, fever and lymphadenopathy. Protection conferred by the vaccine also lasts for only 2–10 years, rather than the longer-lasting immunity that follows natural infection. Most importantly, small amounts of infectious virus typically appear in the nasopharynx 2–3 weeks after immunization, making vaccination very dangerous for pregnant women coming in close contact with a recently vaccinated person or even worse having herself been vaccinated while not knowing she was pregnant.

Vaccines based on synthetic or recombinant peptides would not present this hazard because the antigenic material would be significantly less allergenic or non-allergenic. However, such vaccines are not now available and the immunogenicity and neutralizing properties of peptide-based vaccines are unknown. Furthermore, not all peptides are expected to be useful in vaccines. For example, high antibody titers in HAI tests do not correlate well with protection against rubella infection (Partridge et al., 1981, Br. Med. J. 282, 187–188). This may be due to the fact that epitopes involved in hemagglutination and neutralization are different (Trudel et al., 1982, J. Virol. Methods 5, 191–197). Diagnosis based on the detection of neutralizing antibodies, on the other hand, should have a high predictive value for immune status and prevention of rubella infection or reinfection cases.

These differences are important, not only in evaluating peptide-based vaccines against rubella but in assaying the immune status of patients with respect to rubella infectivity. For example, the "purified" rubella antigens now available are potentially infectious and carry both the hemagglutinating and neutralizing epitopes. Thus, specific tests for immune status using these antigens are questionable, and the antigens used in those vaccines may be infectious.

Considering these problems, we have selected certain peptide sequences on the E1 and E2 proteins of the rubella virus and prepared peptides defined by them. These peptides selected for their ability to bind high levels of antibodies, as measured by an ELISA, are useful in diagnostic tests for rubella infection. Peptides of this invention recognized by neutralizing antibodies are also useful as the active ingredient of a substantially innocuous rubella vaccine.

The E1 antigenicity is independent of its glycosylation (Ho-Terry and Cohen, 1984, Arch. Virol. 79, 139–146). The glycosyl moiety is often responsible for non specific interactions in immunoassays. Therefore the use of synthetic peptide antigens, which are not glycosylated, is attractive.

Antibodies to E2 glycoprotein are more abundant in patients with congenital rubella syndrome. In contrast, antibodies to E1 predominate in most other patients (Katow and Sugiura, 1985, J. Clin. Microbiol. 21, 449–451). Thus, each individual peptide of this invention can be used in the differential diagnosis of rubella infections.

Novel peptides and peptides mixtures are disclosed for use in the screening of blood or body fluids for prior exposure to the rubella virus and in the preparation of a safe, effective vaccine against rubella infections. Peptides of the E2 protein are surprisingly active both in diagnosis, and in stimulating protective antibodies. E1 peptides in admixture with the E2 peptides are the preferred antigens of this invention.

The peptides of this invention are useful in a wide variety of specific binding assays for the detection of antibodies to rubella virus, as immunogens for eliciting antibodies which could then be used for the detection, isolation or purification of rubella antigens. The peptides may also be used in the preparation of vaccines against rubella viral infections.

SUMMARY OF THE INVENTION

The present invention provides for novel peptides corresponding to regions of the E2 glycoproteins of the rubella virus. It also provides for analogues of those peptides and mixtures and combinations of those peptides and analogues. The invention further provides for the mixture of peptides from the E2 proteins with linear or cyclic peptides from the E1 protein of rubella virus.

The peptides of the invention are defined by the following formula: a—Y—b, wherein:

Y is a sequence of at least six amino acids taken as a block from the amino acid sequence of the E2 glycoprotein of a strain of rubella virus that corresponds to $AA_{11}$–$AA_{37}$ of the E2 glycoprotein of a strain of rubella virus, which block maintains the sequence and N terminus to C terminus direction of the native amino acid sequence and analogues thereof, the analogues resulting from conservative substitutions in or modifications to the native amino acid sequence block;

a is selected from the group consisting of:
(i) an amino terminus;
(ii) a sequence of one to eight amino acids; preferably, but not limited to a sequence taken as a block from and maintaining the sequence and N terminus to C terminus direction of that portion of the native amino acid sequence of the E2 glycoprotein immediatly N terminal to Y or conservative substitutions in or modifications thereto;
(iii) a substituent effective to facilitate coupling; and
(iv) a substituent effective to improve the immunogenic or antigenic activity of the peptide; and b is selected from the group consisting of:
(i) a carboxy terminus;
(ii) a sequence of one to eight amino acids; preferably, but not limited to a sequence taken as a block from and maintaining the sequence and N terminus to C terminus direction of that portion of the native amino acid sequence of the E2 glycoportein immediatly C terminal to Y or conservative substitutions in or modifications thereto;
(iii) a substituent effective to faciliate coupling; and
(iv) a substituent effective to improve the immunogenic or antigenic activity of the peptide.

The present invention also provides for a mixture of the peptides from the E2 protein of rubella virus as defined above in admixture with a peptide of the E1 protein of the following formula: a—X—b, wherein:

X is a sequence of at least six amino acids taken as a block from the amino acid sequence of the E1 glycoprotein of a strain of rubella virus that corresponds to $AA_{213}$–$AA_{239}$ of the E1 glycoprotein of the Therien strain of rubella virus, which block maintains the sequence and N terminus to C terminus direction of the native amino acid sequence and analogues thereof, the analogues resulting from conservative substitutions in or modifications to the native amino acid sequence block;

a and b are as defined above.

The invention also provides for a method for detecting the presence of antibodies to rubella antigens, and antibodies immunologically reactive with these peptides.

As will be plain from the following description, these peptides, analogues, mixtures and combinations are useful in a wide variety of diagnostic and preventive methods, means and compositions with respect to the rubella virus and infections caused by it.

BRIEF DESCRIPTION OF THE DRAWINGS

FIG. 1 depicts the amino acid sequence of the E1 glycoprotein of the rubella virus (Therien strain) ($aa_1$–$aa_{481}$, Seq. ID No: 1). The amino acids of the sequence are given using the following single letter code:
A=ala, C=cys, D=asp, E=glu, F=phe, G=gly, H=his, I=ile, K=lys, L=leu, M=met, N=asn, P=pro, Q=gln, R=arg, S=ser, T=thr, V=val, W=trp, Y=tyr.

The designations—EP1, EP2 and EP3—denote the three epitopes identified by Terry et al. and Ho-Terry et al., supra. The designations—BCH-178 and BCH-178 cyclic—enote particular peptides of this invention.

FIG. 2 depicts the amino acid sequence of the E2 glycoprotein of the rubella virus ($aa_1$–$aa_{263}$, Seq. ID No: 2). The designations—BCH-463(Seq. ID. No: 3), BCH-481 (Seq. ID. No: 4) and BCH-933 (Seq. ID. No: 5)—denote peptides of this invention.

On both E1 and E2 sequences, the putative glycosylation sites are indicated as (?).

DESCRIPTION OF THE INVENTION

In this description, we used the amino acid sequence and numbering published by Takkinen et al. (supra) for the E1 and E2 rubella glycoproteins to designate and to depict the particular amino acid sequences of the peptides of this invention. However, these peptides, and their analogues, are useful in the diagnosis and prevention of all strains of the Rubella virus, including, for example, strains Therien, Judith, RA 27/3 and M33. Moreover, peptides characterized by amino acid sequences of the corresponding regions of the E1 and E2 proteins of those strains and their analogues are also included within the scope of this invention and the claims of this application. And the terms "corresponds" and "corresponding" are meant to refer to the native amino acids of those defined regions in any strains of rubella virus.

As will appear obvious to persons skilled in the art, some authors will refer to this particular region of the E2 glycoprotein as amino acid sequence 10 to 36 instead of amino acid 11 to 37. These subjective variations in numerical identifications of the amino acids are also within the scope of the present invention.

This invention also includes analogues of the peptides described above. As used herein "analogues" denote amino acid insertions, deletions, substitutions and modifications at one or more sites in the peptide chain in that portion of it that consists of the block of the naturally occurring rubella amino acid sequences. However, as described above, irrespective of such insertions, deletions, substitutions and modifications, the peptides of this invention must contain a sequence of at least six amino acids taken in sequence "as a block" from, for example, $AA_{213}$–$AA_{239}$ of the E1 glycoprotein, or at least six amino acids taken as a block from, for example, $AA_{11}$–$AA_{37}$ of the E2 glycoprotein of a strain of the rubella virus. The term analogue also means any peptide that will possess the same or substantially the same immunoreactivity.

Preferred modifications and substitutions to the native amino acid sequence block in the peptide chain are conservative ones (i.e., those having minimal influence on the secondary or tertiary structure and hydropathic nature of the peptide). These include substitutions such as those described by Dayhoff in the Atlas of Protein Sequence and Structure 5, 1978 and by Argos in EMBO J. 8, 779–785, 1989. For example, amino acids belonging to one of the following groups represent conservative changes:

ala, pro, gly, glu, asp, gln, asn, ser, thr;
cys, ser, tyr, thr;
val, ile, leu, met, ala, phe;
lys, arg, his; and
phe, tyr, trp, his.

In like manner, methionine, an amino acid which is prone to oxidation may be replaced by norleucine. They also include substitutions of D isomers for the corresponding L amino acids.

Of course, also included within the scope of the present invention are modifications to the native amino acid sequence that appear naturally in certain strains of rubella. For example, one Therien strain of rubella (accession #P07566) possesses a cysteine instead of an arginine at position 19 of the E2 glycoprotein (see FIG. 2).

The term "amino acid" as employed in this description (e.g., in the definition of a and b) except when referring to the amino acids taken as a block from the E1 or E2 glycoproteins of the rubella virus, encompasses all of the natural amino acids, those amino acids in their D- configurations, and the known non-native, synthetic, and modified amino acids, such as homocysteine, ornithine and norleucine.

Illustrative of the peptides of this invention are peptides wherein Y is an amino acid sequence that corresponds to the sequence $AA_{11}$–$AA_{37}$ of the E2 glycoprotein of rubella strains and analogues thereof.

Illustrative of the peptides of this invention are the following E2 glycoprotein derived peptides:
BCH-463: a-TLPQPPRAHGQHYGHHHHQL-b (Therien strain) (Seq. ID. No: 3)
BCH-481: a-APPTLPQPPRAHG-QHYGHHHHQLPFLG-b (Therien strain) (Seq. ID. No: 4)
BCH-933: a-AppMPPQPPRAHG-QHYGHHHHQLPFLG-b (RA 27/3 strain) (Seq. ID. No: 5)
and analogues thereof, wherein a and b are as defined above.

The most preferred E2 glycoprotein derived-peptide of this invention (using the Therien strain for ease of reference ) is:
BCH-481: a-APPTLPQPPRAHG-QHYGHHHHQLPFLG-b (Therien strain) (Seq. ID. No: 4)
and analogues thereof, wherein a and b are as defined above.

The E1 peptides used in admixture with the E2 peptides of this invention as defined in these formulae may be linear or cyclic. We, however, prefer cyclic peptides for both diagnostic uses and as the active components of the vaccines of this invention.

The preferred E1 glycoprotein derived-peptide (using amino acid sequences of the Therien strain for ease of references) to be used in admixture with the E2 peptides is the following:
BCH-178: a-NQQSRWGLGSPNCHGPDWASPVCQRHS-b (Seq. ID. No: 6)
and analogues thereof, wherein a and b are as defined above.

The most preferred E1 peptide of this invention (using the Therien strain for ease of reference) is:

BCH-178 cyclic: a-NQQSRWGLGSPNCHGPDWASPVCQRHS-b (SEQ ID NO: 7)

and analogues thereof, wherein a and b are as defined above.

Also within the scope of the present invention are combinations or mixtures of the cyclic and linear synthetic peptides of this invention. For example, a preferred peptide mixture for the detection of antibodies specific to the rubella virus comprises synthetic peptide BCH-481 (Seq. ID. No: 4) or analogues thereof and any other peptide of this invention. A more preferred peptide mixture of the invention comprises synthetic peptides BCH-481 (Seq. ID. No: 4), BCH-933 (Seq. ID. No: 5) and BCH-178 cyclic (Seq. ID. No: 6) and analogues thereof. A most preferred peptide mixture for the detection of antibodies specific to the rubella virus comprises synthetic peptides BCH-481 (Seq. ID. No: 4) and BCH-178 (Seq. ID. No: 7) cyclic or analogues thereof.

It may also be desirable to covalently join two or more peptide sequences of this invention or even to form a polymer consisting of two or more peptides of this invention. Such changes may facilitate passive adsorption of the peptides to a solid surface without loss of their antigenic properties. It may also be desirable to covalently join one or more synthetic peptides of this invention with a synthetic peptide known to carry a T-cell epitope, the resulting conjugate being more useful as an immunogen.

An unexpected advantage of the novel peptide mixture of this invention is that it is capable of providing complete detection of rubella-specific antibodies derived from a panel of 886 serum samples taken from 443 patients prior to and following their rubella vaccination. Mixture consisting of peptides BCH-481 (Seq. ID. No: 4) and BCH-178 cyclic (Seq. ID. No: 7) is the most preferred example of mixtures having this advantage.

Another advantage of the peptides of this invention is the high level of specificity displayed by them. This results in a minimal number of false positives. The use of BCH-178 (Seq. ID. No: 7) and BCH-481 (Seq. ID. No: 4) in a mixture helps in detecting anti-rubella antibodies specific for both E1 and E2 proteins. In contrast, by using each of these peptides individually, we can detect separately each of the anti-rubella antibody and this then helps in determining a person's immune status to rubella, reactivity towards BCH-178c being a better indication of protection.

As described above by a and b, it is often useful and is within the scope of this invention to modify the peptide block consisting of the naturally occurring rubella amino acid sequences in the peptides of this invention in order to make the chosen peptide more useful as an immunodiagnostic reagent or as an active ingredient of a vaccine. Such changes, for example, include:
addition of a cysteine residue to one or both terminals in order to facilitate coupling of the peptide to a suitable carrier with heterobifunctional cross-linking reagents such as sulfosuccinimidyl-4-(p-maleimidophenyl) butyrate (a preferred reagent for effecting such linkages), sulfosuccinimidyl-4-(N-maleimidomethyl) cyclohexane- 1-carboxylate or N-succinimidyl-3- (2-pyridyldithio) propionate;
addition of 1 to 8 additional amino acids at one or both terminals of the peptide to facilitate linking of the peptides to each other, for coupling to a support or larger peptide or protein or for modifying the physical or chemical properties of the peptide. Examples of such changes may be effected by addition of tyrosine, glutamic acid or aspartic acid which can be used as linkers via an esterification reaction or lysine which can be linked via Schiff's base or amide formation. As described above such additional amino acids include all of the natural amino acids, those amino acids in their D- configurations. synthetic and modified amino acids;
and
derivatization of one or both terminals of the peptide by, for example, acylation or amidation. These modifications result in changes in the net charge on the peptide and can also facilitate covalent linking of the peptide to a solid support, a carrier or another peptide. Examples of the substituents effective to facilitate coupling or to improve the immunogenicity or antigenic activity of the peptide are $C_2$–$C_{16}$ acyl groups, polyethylene glycol and phospholipids.

To prepare the novel peptides of this invention any of the conventional peptide production methodologies may be used. These include synthesis, recombinant DNA technology and combinations thereof. Solid phase synthesis is preferred but the other methods also work. In that synthetic approach, the resin support may be any suitable resin conventionally employed in the art for the solid phase preparation of peptides. Preferably, the resin is p- benzyloxyalcohol polystyrene or p-methylbenzydrylamine resin. Following the coupling of the first protected amino acid to the resin support, the amino protecting group is removed by standard methods conventionally employed in the art. After the removal of the amino protecting group, the remaining α-amino protected and, if necessary, side chain protected amino acids are coupled, sequentially, in the desired order to obtain the chosen peptide. Alternatively, multiple amino acid groups may be coupled using solution methodology, prior to coupling with the resin-supported amino acid sequence.

The selection of an appropriate coupling reagent follows established art. For instance, suitable coupling reagents are N,N'-diisopropyl- carbodiimide or N,N'-dicyclohexylcarbodiimide (DCC) or benzotriazol-1-yloxy-tris (dimethylamino) phosphonium hexafluorophosphate either alone or preferably in the presence of 1-hydroxybenzotriazole. Another useful coupling procedure employs preformed symmetrical anhydrides of protected amino acids.

The necessary α-amino protecting group employed for each amino acid introduced onto the growing polypeptide chain is preferably 9-fluorenylmethyloxycarbonyl (FMOC), although any other suitable protecting group may be employed as long as it does not degrade under the coupling reaction conditions. The protecting group should also be readily removable selectively in the presence of any other protecting group already present in the growing peptide chain.

The criteria for selecting protecting groups for the side chain amino acids are: (a) stability of the protecting group to the various reagents under reaction conditions selective for the removal of the α-amino protecting group at each step of the synthesis; (b) retention of the protecting group's strategic properties (i.e., it should not be split off under coupling conditions) and (c) easy removability of protecting group upon conclusion of the peptide synthesis and under conditions that do not otherwise affect the peptide structure.

The fully protected resin-supported peptides are preferably cleaved from the p-benzyloxy alcohol resin with a 50% to 60% solution of trifluoroacetic acid in methylene chloride for 1 to 6 hours at room temperature in the presence of appropriate scavengers such as, anisole, thioanisole, ethylmethylsulfide, 1,2-ethanedithiol and related reagents. Simultaneously, most acid labile side-chain protecting groups are removed. More acid-resistant protecting groups are typically removed by HF treatment.

Cyclic peptides may be prepared from the linear peptides of this invention by any of the well-known synthetic cyclization methodologies. Preferably, two existing thiol containing residues, such as cysteine, are employed. However, a thiol residue may, instead, be substituted for a non-thiol residue to effect cyclization. For example, the cyclic synthetic peptides of this invention may be prepared by the direct oxidative conversion of protected or unprotected SH-groups to a disulfide bond by techniques generally known in the art of peptide synthesis. The preferred method involves the direct oxidation of free SH-groups with potassium ferricyanide. Alternatively, cyclization may be effected using substituents a and b.

The peptides of the present invention are useful as diagnostic reagents for the detection and quantification of rubella virus-associated antibodies in accordance with methods well known in the art. These include enzyme immunoassay (EIA) such as ELISA, radio immunoassay (RIA), fluorescence activated immunoassay (FIA), hemagglutination, latex agglutination, single-dot and multi-dot methods and assays.

A preferred convenient and classical technique for the determination of antibodies against the rubella virus using a peptide or a peptide mixture or combination of this invention is an enzyme-linked immunosorbent assay (ELISA). In this assay, for example, a peptide or a peptide mixture or combination of this invention is adsorbed onto, or covalently coupled to, the wells of a microtiter plate. The wells are then treated with the sera or analyte to be tested. After washing, a solution of anti-human IgG or anti-human IgM antibodies labeled with peroxidase is added. The determination of the peroxidase is performed with a corresponding substrate, e.g., 3,3', 5, 5'-tetra- methylbenzidine. Without departing from the usefulness of this illustrative assay, the peroxidase can be exchanged by another label, e.g., by a radioactive, fluorescent, chemiluminescent or infra-red emitting label.

Another method for the determination of antibodies against rubella virus with the peptides of this invention is an enzyme immunological test according to the so-called "Double-Antigen-Sandwich Assay". This method is based on the work of Maiolini, as described in Immunological Methods, 20, 25–34, 1978. According to this method, the serum or other analyte to be tested is contacted with a solid phase on which a peptide of this invention has been coated (capture layer) and with a peptide of this invention which has been labeled with peroxidase (probe layer). The immunological reaction can be performed in one or two steps. A washing step is typically carried out between the two incubation steps and at the end of incubation time. Thereafter, the peroxidase is determined, e.g., using o-phenylene diamine. Other enzymes and chromogens, including those already described, can also be employed in this assay.

Suitable solid phases for use in the above-described assays and assay methods include organic and inorganic polymers, e.g., amylases, dextrans, natural or modified celluloses, polyethylene, polystyrene, polyacrylamides, agaroses, magnetite, porous glass powder, polyvinylidene fluoride (Kynar* ) and latex, the inner wall of test vessels (i.e., test tubes, titer plates or cuvettes of glass or artificial material) as well as the surface of solid bodies (i.e., rods of glass and artificial material, rods with terminal thickening, rods with terminal lobes or lamallae). Spheres of glass \* denotes a trade mark and artificial material are especially suitable as solid phase carriers.

The peptides of this invention and the mixtures and combinations of them are useful in the determination and quantification of antibodies against rubella virus. These peptides are also useful for the determination and quantification of rubella virus antigens themselves. These peptides either free, polymerized or conjugated to an appropriate carrier, are useful in eliciting antibodies immunologically reactive to the antigens of the rubella virus. Monoclonal antibodies are particularly preferred for this purpose. Suitable antibodies can be produced by injecting a mammalian or avian animal with a sufficient amount of the peptide to elicit the desired immune response and recovering those antibodies from the serum of treated animals. Suitable host animals for eliciting antibodies include, for example, rabbits, horses, goats, guinea pigs, rats, mice, cows, sheeps and hens. Preferably, hybridomas producing the desired monoclonal antibodies are preferably prepared using the peptides of this invention .and conventional techniques. For example, the well-known Kohler and Milstein technique for producing monoclonal antibodies may be used. In order to distinguish monoclonal antibodies which are directed against the same antigen, but against different epitopes, the method of Stähli et al. (J. of Immunol. Methods, 32,297–304, 1980) can be used.

Various methods can be employed in the determination or quantification of the rubella virus or a portion thereof using the above antibodies. These are known in the prior art. In one such procedure, known amounts of a serum sample or other analyte to be assayed are mixed together with a radio labeled linear or cyclic peptide of this invention or a mixture or combination of those peptides and an unlabeled peptide of this invention or a mixture or combination thereof. A given amount of an anti-peptide, preferably a monoclonal antibody, is also added and the mixture allowed to stand. The resulting antibody/antigen complex is then separated from the unbound reagents by procedures known in the art, for example by treatment with ammonium sulfate, polyethylene glycol, and a second antibody either in excess or bound to an insoluble support, or dextran-coated charcoal. The concentration of the labeled peptide is then determined in either the bound or unbound phase and the rubella virus antigen content of the sample determined by comparing the level of labeled component to a standard curve in a manner known per se.

Another suitable method for using these antibodies in assays is the "Double-Antibody-Sandwich Assay". According to this assay, the sample to be tested is treated with two different antibodies, e.g., raised by immunizing different animals, e.g., sheep and rabbits with a peptide of this invention or a mixture or combination thereof. One of the antibodies is labeled and the other is coated on a solid phase. The preferred solid phase is a plastic bead and the preferred label is horseradish peroxidase.

Typically in the "Double-Antibody-Sandwich Assay", the sample is incubated with the solid phase bound-antibody and the labeled antibody. However, it is also possible to contact the sample first with the bound-antibody and, then after an optional washing, to contact the sample with the labeled antibody. Preferably, however, the sample is treated simultaneously with the solid phase and the labeled antibody together. After the immunological reaction(s), the mixture is washed and the label is determined according to procedures known in the art. In the case where peroxidase is used as the label, the determination maybe performed using a substrate, e.g., with o-phenylene diamine or with tetramethylbenzidine. The amount of the labeled component is proportional to the amount of the antigen(s) present in the analyte or serum sample.

The methods and assays for the determination and quantification of rubella virus antigens or antibodies against that virus, as described above, can be conducted in suitable test kits comprising, in a container, a peptide of this invention, mixtures or combinations thereof, or antibodies against rubella virus elicited by a those peptides or mixtures and combinations thereof.

The peptides of this invention and mixtures and combinations thereof are also useful as the active component of vaccines capable of inducing protective immunity against the rubella virus in hosts susceptible to infection with that virus. Routes of administration, antigen doses, number and frequency of injections will vary from individual to individual and may parallel those currently being used in providing immunity to other viral infections. For example, the vaccines of this invention are pharmaceutically acceptable compositions containing at least one peptide of this invention, its analogues or mixtures or combinations thereof, in an amount effective to raise antibodies in a mammal, including a human, treated with that composition. These antibodies should be sufficient to protect the treated mammal from a rubella viral infection for a period of time.

The vaccines are prepared in accordance with known methods. The vaccine compositions of this invention are conveniently and conventionally combined with physiologically acceptable carriers, such as pharmaceutical grade saline, tetanus toxoid, and keyhole limpet hemocyanin. The vaccine compositions of this invention may also contain adjuvants or other enhancers of immune response, such as alum preparations, liposomes or immunomodulators. Furthermore, these vaccine compositions may comprise other antigens to provide immunity against other viruses (e.g., mumps and measles) or pathogens in addition to rubella. The amount of these other antigens is again dependent on the mammal to be treated and the course of the disease. However, the antigen should be present in an amount effective to raise antibodies sufficient to protect the treated mammal from that pathogen or virus for a period of time.

The peptides of the present invention may also be useful for what is referred to as "spiking" by persons skilled in the art. The peptides may therefore be admixed with recombinant or any other rubella antigens to enhance the immunogenic response or antigenic activity of the vaccine or diagnostic tests respectively.

EXAMPLES

General procedures for the synthesis and utilization of the peptides of this invention are provided below.

Procedure 1: Preparation of Resins Carrying the N-FMOC Protected Amino Acid Residue The desired N-FMOC protected amino acid residue in a mixture of methylene chloride ($CH_2Cl_2$) and dimethylformamide (DMF) (4:1) was added to a suspension of p-benzyloxy alcohol resin in $CH_2Cl_2$:DMF (4:1) at 0° C. The mixture was stirred manually for a few seconds and then treated with N,N'-dicyclohexyl- carbodiimide (DCC) followed by a catalytic amount of 4-(dimethylamino) pyridine. The mixture was stirred at 0° C. for an additional 30 minutes and then at room temperature overnight. The filtered resin was washed successively with $CH_2Cl_2$, DMF and isopropanol (3 washes each) and finally, with CH$_2$Cl$_2$. The resin was suspended in CH$_2$Cl$_2$, chilled in an ice bath and redistilled pyridine was added to the stirred suspension followed by benzoyl chloride. Stirring was continued at 0° C. for 30 minutes and then at room temperature for 60 minutes. After filtration, the resin was washed successively with CH$_2$Cl$_2$, DMF and isopropanol (3 washes each) and finally with petroleum ether (twice) before being dried under high vacuum to a constant weight. Spectrophotometric determination of substitution according to Meienhofer et al. (Int. J. Peptide Protein Res., 13, 35, 1979) indicates the degree of substitution on the resin.

Procedure 2: Coupling of Subsequent Amino Acids

The resin carrying the N-FMOC protected first amino acid residue was placed in a reaction vessel of a Biosearch 9600 Peptide Synthesizer* and treated as follows:
* denotes a trade mark 1) Washed with DMF (4 times for 20 sec. each)
2) Prewashed with a 30% solution of piperidine in DMF (3 min.)
3) Deprotected with a 30% solution of piperidine in DMF (7 min.)
4) Washed with DMF (8 times for 20 sec. each)
5) Checked for free amino groups—Kaiser Test (must be positive)
6) The peptide resin was then gently shaken for 1 or 2 hrs with 8 equivalents of the desired FMOC-protected amino acid and 1-hydroxybenzotriazole and benzotriazol-1-yloxy- tris (dimethyl-amino) phosphonium hexafluorophosphate all dissolved in dry redistilled DMF containing 16 equivalents of 4-methylmorpholine.
7) Washed with DMF (6 times for 20 sec. each)

After step 7, an aliquot was taken for a ninhydrin test. If the test was negative, one goes back to step 1 for coupling of the next amino acid. If the test was positive or slightly positive, steps 6 and 7 should be repeated.

The above scheme may be used for coupling each of the amino acids of the peptides described in this invention. N-protection with FMOC may also be used with each of the remaining amino acids throughout the synthesis.

Radiolabeled peptides may be prepared by the incorporation of a tritiated amino acid using the above coupling protocol.

After the addition of the last amino acid, the N-FMOC of the N-terminal residue is removed by going back to steps 1-7 of the above scheme. The peptide resin is washed with CH$_2$Cl$_2$ and dried in vacuo to give the crude protected peptide.

Procedure 3: Deprotection and Cleavage of the Peptides from the Resin

The protected peptide-resin was suspended in a 55% solution of trifluoroacetic acid (TFA) in CH$_2$Cl$_2$, containing 2.5% ethanedithiol and 2.5% anisole. The mixture was flushed with N$_2$ and stirred for 1.5 hours at room temperature. The mixture was filtered and the resin washed with CH$_2$Cl$_2$. The resin was treated again with 20% TFA in CH$_2$Cl$_2$ for 5 minutes at room temperature. The mixture was filtered and the resin washed with 20% TFA in CH$_2$Cl$_2$ and then washed with CH$_2$Cl$_2$. The combined filtrates were evaporated in vacuo below 35° C. and the residue triturated several times with dry dimethyl ether. The solid was dissolved in 10% aqueous acetic acid and lyophilized to afford the crude product.

The peptides containing arginine and cysteine residues were further de protected by HF treatment at 0° C. for 1 hour in the presence of anisole and dimethylsulfide. The peptides were extracted with 10% aqueous acetic acid, washed with dimethyl ether and lyophilized to afford the crude peptides.

Procedure 4: Purification of Peptides

The crude peptides were purified by preparative HPLC on a Vydac* column (2.5×25 mm) of C$_{18}$ or C$_4$ reverse phase with a gradient of the mobile phase. The effluent was monitored at 220 nm and subsequently by analytical HPLC. Relevant fractions were pooled, evaporated and lyophilized. The identity of the synthetic peptides was verified by analytical reverse phase chromatography and by amino acid analysis.
* denotes a trade mark Procedure 5: Cyclization of Peptides A solution of potassium ferricyanide (0.01M, pH 7.0) was added slowly to a dilute aqueous solution (0.5 mM) of the linear peptide at pH 7.0. After 24 hours at room temperature, the pH was lowered to 5.0 and the solution treated with ion exchange resin (Bio-Rad* Ag-3-X4a, Cl-form) for 30 minutes. The suspension was filtered and the filtrate lyophilized to give the crude cyclic peptide. The peptide was purified by preparative reverse phase HPLC and characterized by amino acid analysis. Proof of cyclicity was obtained by comparing the HPLC mobility of the cyclic peptide with the starting linear peptide by reducing an aliquot of the cyclic peptide back to the linear peptide and also by observing the
* denotes a trade mark disappearance of free sulfhydryl groups (Ellman's test) after the cyclization.

Procedure 6: Conjugation of Peptides to Bovine Serum Albumin or Keyhole Limpet Hemocyanin Peptides were conjugated to BSA or KLH previously derivatized with either sulfosuccinimidyl 4-(p-maleimidophenyl ) butyrate (Sulfo-SMPB) or sulfosuccinimidyl 4-(N-maleimidomethyl) cyclohexane-1-carboxylate (Sulfo-SMCC).

An aqueous solution of sulfo-SMPB or sulfo-SMCC (Pierce Chemicals) was added to a solution of BSA or KLH in 0.02M sodium phosphate buffer (pH 7.0). The mixture was shaken at room temperature for 45 minutes and the activated carrier immediately applied to a Sephadex G-25* column equilibrated with 0.1M sodium phosphate buffer (pH 6.0) at 4° C.
* denotes a trade mark The fractions of the first peak absorbance (280 nm) corresponding to activated carrier were combined in a round bottom flask to which was added a solution of peptide in 0.05M sodium phosphate buffer (pH 6.2). The mixture was thoroughly flushed with N$_2$ and incubated overnight at room temperature. The coupling efficiency was monitored using $^3$H-labeled peptide and by amino acid analysis of the conjugate.

Procedure 7: Detection of Antibodies to Rubella Virus by an Enzyme Linked Immunosorbent Assay (ELISA)

Each well of the microtiter plate was coated with 100 μl of a solution containing a peptide (5 μg/ml) or mixture of peptides (10 μg/ml) and left overnight. The wells were emptied and washed twice with a washing buffer (Tris, 0.043M; NaCl, 0.5M; thimerosal, 0.01% w/v; Tween* 20, 0.05% v/v; pH 7.4). The wells were then saturated with 0.35 ml of washing buffer for 1 hour at 37° C. and washed once with the same buffer. Serum samples to be analyzed were diluted with specimen buffer (washing buffer plus casein, 0.05% w/v). The wells were rinsed with washing buffer prior to the addition of the diluted serum sample (0.1 ml). These were left to incubate for 1 hour at room temperature. The wells were then emptied, washed twice rapidly and then once for two minutes with washing buffer. The conjugate solution (peroxidase- labeled affinity-purified goat antibody to human IgG, 0.5 mg in 5 ml 50% glycerol) diluted with 1% w/v bovine serum albumin in washing buffer was added to each well (0.1 ml) and incubated for 1 hour at room temperature.. The wells were then emptied and washed five times with the washing buffer. The substrate solution (3,3', 5,5'-tetramethylbenzidine, 8 mg per ml of DMSO) was diluted with 100 volumes 0.1M citrate-acetate buffer (pH 5.6) containing 0.1% v/v of 30% $H_2O_2$ and added to each well (0.1 ml per well). After 10 minutes, the contents of each well were treated with 0.1 ml 2N $H_2SO_4$ and the optical density read at 450 nm. All determinations were done in

* denotes a trade mark duplicate.

Using general procedures substantially as described above the following specific peptides were prepared: BCH-178 (Seq. ID. No: 6), BCH-178 cyclic (Seq. ID. No: 7), BCH-463 (Seq. ID. No: 3) and BCH-481 (Seq. ID. No: 4).

These peptides were then evaluated for their ability to detect rubella-specific antibodies.

Experiment 1

In Experiment 1 peptides BCH-178 cyclic, BCH-463, BCH-481 (Seq. ID. No: 4) and mixture of BCH-178 cyclic (Seq. ID. No: 7) and BCH-463 (Seq. ID. No: 3(Seq. ID. No: 3) or BCH-481 (Seq. ID. No: 4) were compared in ELISA assays using a panel of seropositive and seronegative serum and plasma samples obtained from a variety of Canadian, US and European sources.

The results are displayed in Table 1 as a ratio of sample absorbancy to cutoff absorbancy (0.2). The value above which a sample is considered positive for the presence of rubella antibodies was defined as being equal or superior to one (1.0).

These results demonstrate the superiority of the mixture of BCH-481 (Seq. ID. No: 4) and BCH-178 (Seq. ID. No: 7) cyclic as completed to each peptides separately.

Experiment 2

In experiment 2, a mixture of synthetic peptides (BCH-178 cyclic (Seq. ID. No: 7) and BCH-481(Seq. ID. No: 4)) is employed in an assay for the detection of rubella-specific antibodies. The results are compared to those obtained with two commercial viral lysate-based rubella kits (Table 2a and 2b). The results obtained with the mixture of BCH-481 (Seq. ID. No: 4) and BCH-178 cyclic (Seq. ID. No: 7) are substantially equivalent to the results obtained with a viral lysate-based test (Enzygnost). Our simple peptide mixture is thus capable of replacing a more complex commercially available kit and provide the user with similar results. With the peptide mixture, there is the added advantage of not having to run the test in parallel on a control well.

Experiment 3

In experiment 3, we evaluated the use of mixture of the rubella antigens BCH-481 (Seq. ID. No: 4) and BCH-178 cyclic (Seq. ID. No: 7) to detect anti-rubella antibodies present in 476 serum samples from a pediatric hospital. The serum samples were tested with no preselection (on a routine rubella testing basis) and the results were compared to those obtained with 3 other commercial rubella kits (Abbott, Behring and Diamedix). All the techniques were performed and results interpreted as described by their manufacturer. The Behring's Enzygnost EIA assay defines a "gray zone" of indeterminate reactivity. Samples which fall in the gray zone were discarded for ease of results comparison.

Table 3 displays the capacity of each technique to distinguish between positive and negative samples of 476 serum samples. It shows that results obtained with the peptide mixture of the present invention is in agreement with those obtained with three commercially available kits; correlation ranges between 97.3%, and 95.%.

While we have herein before described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented herein before by way of example.

TABLE 1

| SAMPLE ID | BCH178c (SEQ ID NO: 7) | BCH463 (SEQ ID NO: 3) | BCH481 (SEQ ID NO: 4) | BCH178c (SEQ ID NO: 7) BCH463 (SEQ ID NO: 3) | BCH178c (SEQ ID NO: 7) BCH481 (SEQ ID NO: 4) |
|---|---|---|---|---|---|
| 75 | 0.6 | 0.5 | 0.7 | 0.45 | 0.95 |
| 78 | 0.75 | 0.48 | 0.5 | 0.5 | 1.35 |
| 85 | 0.70 | 0.4 | 0.4 | 0.45 | 1.05 |
| 144 | 0.45 | 2.45 | 8.95 | 1.39 | 9.3 |
| 143 | 0.35 | 3.2 | 11.9 | 1.88 | 12.75 |
| 1025 | 0.3 | 3.74 | 12.35 | 2.45 | 13.05 |
| 151 | 0.6 | 1.7 | 6.75 | 1.16 | 6.75 |
| 1026 | 0.2 | 1.28 | 5.85 | 0.76 | 5.85 |
| 152 | 0.65 | 0.5 | 0.75 | 0.35 | 0.65 |
| 156 | 0.35 | 1.7 | >14 | 0.66 | >14 |
| 1027 | 0.2 | 1.25 | >14 | 0.58 | 10.85 |
| 171 | 0.6 | 0.69 | 2.2 | 0.67 | 2.75 |
| 196 | 0.55 | 0.51 | 0.7 | 0.57 | 1.15 |
| 197 | 0.8 | 0.48 | 0.6 | 0.63 | 1.2 |
| 279 | 0.65 | 1.01 | 4.1 | 0.54 | 3.75 |
| 330 | 0.35 | 0.7 | 2.15 | 0.68 | 2.1 |

TABLE 1-continued

| SAMPLE ID | BCH178c (SEQ ID NO: 7) | BCH463 (SEQ ID NO: 3) | BCH481 (SEQ ID NO: 4) | BCH178c (SEQ ID NO: 7) BCH463 (SEQ ID NO: 3) | BCH178c (SEQ ID NO: 7) BCH481 (SEQ ID NO: 4) |
|---|---|---|---|---|---|
| 333 | 0.75 | 0.88 | 4.0 | 0.655 | 4.5 |

TABLE 2

| ENZYGNOST-IgG | BCH-178 (SEQ ID NO: 7) NEG. | BCH-178 POS. | BCH-481 (SEQ ID NO: 4) NEG. | BCH-481 POS. | COCKTAIL BCH-178-481 (SEQ ID NO: 7) NEG. | COCKTAIL POS. | TOTAL |
|---|---|---|---|---|---|---|---|
| a. (Pre-vaccination samples) (n = 443) | | | | | | | |
| NEGATIVE | 170 | 22 | 175 | 17 | 161 | 31 | 192 |
| INDETERMINATE | 14 | 11 | 20 | 5 | 10 | 15 | 25 |
| POSITIVE | 38 | 188 | 70 | 156 | 12 | 214 | 226 |
| TOTAL | 222 | 221 | 265 | 178 | 183 | 260 | 443 |
| b. (Post-vaccination samples) (n = 443) | | | | | | | |
| NEGATIVE | 1 | 2 | 2 | 1 | 1 | 2 | 3 |
| INDETERMINATE | — | 1 | — | 1 | — | 1 | 1 |
| POSITIVE | 30 | 409 | 53 | 386 | 4 | 435 | 439 |
| TOTAL | 31 | 412 | 55 | 388 | 5 | 438 | 443 |

TABLE 3

| Other tests | BioChem Detect-Rubella E1E2 (BCH-178c + BCH-481) (SEQ ID NOS: 7 and 4) Negative/Positive/Agreement | | |
|---|---|---|---|
| Abbott | | | |
| Negative | 26 | 2 | |
| Positive | 15 | 433 | 96.4% |
| Diamedix | | | |
| Negative | 33 | 5 | |
| Positive | 8 | 430 | 97.3% |
| Behring | | | |
| Negative | 34 | 17 | |
| Indeterminate | 1 | 15 | |
| Positive | 6 | 403 | 95% |

---

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 481 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
      ( A ) ORGANISM: E1 Glycoprotein
      ( B ) STRAIN: Therien strain ( i x ) FEATURE:
      ( A ) NAME/KEY: Protein
      ( B ) LOCATION: 1..481

( x i ) SEQUENCE DESCRIPTION: SEQ ID NO:1:

```
Glu Glu Ala Phe Thr Tyr Leu Cys Thr Ala Pro Gly Cys Ala Thr Gln
 1               5                  10                  15

Ala Pro Val Pro Val Arg Leu Ala Gly Val Arg Phe Glu Ser Lys Ile
                20                  25                  30

Val Asp Gly Gly Cys Phe Ala Pro Trp Asp Leu Glu Ala Thr Gly Ala
            35                  40                  45
```

| | | | | | | | | | | | | | | |
|---|---|---|---|---|---|---|---|---|---|---|---|---|---|---|
| Cys | Ile | Cys | Glu | Ile | Pro | Thr | Asp | Val | Ser | Cys | Glu | Gly | Leu | Gly | Ala |
| | 50 | | | | 55 | | | | | 60 | | | | |
| Trp | Val | Pro | Ala | Ala | Pro | Cys | Ala | Arg | Ile | Trp | Asn | Gly | Thr | Gln | Arg |
| 65 | | | | | 70 | | | | 75 | | | | | | 80 |
| Ala | Cys | Thr | Phe | Trp | Ala | Val | Asn | Ala | Tyr | Ser | Ser | Gly | Gly | Tyr | Ala |
| | | | | 85 | | | | | 90 | | | | | 95 | |
| Gln | Leu | Ala | Ser | Tyr | Phe | Asn | Pro | Gly | Gly | Ser | Tyr | Tyr | Lys | Gln | Tyr |
| | | | | 100 | | | | | 105 | | | | 110 | | |
| His | Pro | Thr | Ala | Cys | Glu | Val | Glu | Pro | Ala | Phe | Gly | His | Ser | Asp | Ala |
| | | | 115 | | | | 120 | | | | | 125 | | | |
| Ala | Cys | Trp | Gly | Phe | Pro | Thr | Asp | Thr | Val | Met | Ser | Val | Phe | Ala | Leu |
| | 130 | | | | | 135 | | | | 140 | | | | | |
| Ala | Ser | Tyr | Val | Gln | His | Pro | His | Lys | Thr | Val | Arg | Val | Lys | Phe | His |
| 145 | | | | | 150 | | | | | 155 | | | | | 160 |
| Thr | Glu | Thr | Arg | Thr | Val | Trp | Gln | Leu | Ser | Val | Ala | Gly | Val | Ser | Cys |
| | | | | 165 | | | | | 170 | | | | | 175 | |
| Asn | Val | Thr | Thr | Glu | His | Pro | Phe | Cys | Asn | Thr | Pro | His | Gly | Gln | Leu |
| | | | 180 | | | | | 185 | | | | | 190 | | |
| Glu | Val | Gln | Val | Pro | Pro | Asp | Pro | Gly | Asp | Leu | Val | Glu | Tyr | Ile | Met |
| | | 195 | | | | | 200 | | | | | 205 | | | |
| Asn | Tyr | Thr | Gly | Asn | Gln | Gln | Ser | Arg | Trp | Gly | Leu | Gly | Ser | Pro | Asn |
| | 210 | | | | | 215 | | | | | 220 | | | | |
| Cys | His | Gly | Pro | Asp | Trp | Ala | Ser | Pro | Val | Cys | Gln | Arg | His | Ser | Pro |
| 225 | | | | | 230 | | | | | 235 | | | | | 240 |
| Asp | Cys | Ser | Arg | Leu | Val | Gly | Ala | Thr | Pro | Glu | Arg | Pro | Arg | Leu | Arg |
| | | | | 245 | | | | | 250 | | | | | 255 | |
| Leu | Val | Asp | Ala | Asp | Asp | Pro | Leu | Leu | Arg | Thr | Ala | Pro | Gly | Pro | Gly |
| | | | | 260 | | | | | 265 | | | | | 270 | |
| Glu | Val | Trp | Val | Thr | Pro | Val | Ile | Gly | Ser | Gln | Ala | Arg | Lys | Cys | Gly |
| | | | 275 | | | | | 280 | | | | | 285 | | |
| Leu | His | Ile | Arg | Ala | Gly | Pro | Tyr | Gly | His | Ala | Thr | Val | Glu | Met | Pro |
| | | 290 | | | | | 295 | | | | | 300 | | | |
| Glu | Trp | Ile | His | Ala | His | Thr | Thr | Ser | Asp | Pro | Trp | His | Pro | Pro | Gly |
| 305 | | | | | 310 | | | | | 315 | | | | | 320 |
| Pro | Leu | Gly | Leu | Lys | Phe | Lys | Thr | Val | Arg | Pro | Val | Ala | Leu | Pro | Arg |
| | | | | 325 | | | | | 330 | | | | | 335 | |
| Thr | Leu | Ala | Pro | Pro | Arg | Asn | Val | Arg | Val | Thr | Gly | Cys | Tyr | Gln | Cys |
| | | | 340 | | | | | 345 | | | | | 350 | | |
| Gly | Thr | Pro | Ala | Leu | Val | Glu | Gly | Leu | Ala | Pro | Gly | Gly | Gly | Asn | Cys |
| | | 355 | | | | | 360 | | | | | 365 | | | |
| His | Leu | Thr | Val | Asn | Gly | Glu | Asp | Val | Gly | Ala | Val | Pro | Pro | Gly | Lys |
| | 370 | | | | | 375 | | | | | 380 | | | | |
| Phe | Val | Thr | Ala | Ala | Leu | Leu | Asn | Thr | Pro | Pro | Pro | Tyr | Gln | Val | Ser |
| 385 | | | | | 390 | | | | | 395 | | | | | 400 |
| Cys | Gly | Gly | Glu | Ser | Asp | Arg | Ala | Ser | Ala | Arg | Val | Ile | Asp | Pro | Ala |
| | | | | 405 | | | | | 410 | | | | | 415 | |
| Ala | Gln | Ser | Phe | Thr | Gly | Val | Val | Tyr | Gly | Thr | His | Thr | Thr | Ala | Val |
| | | | 420 | | | | | 425 | | | | | 430 | | |
| Ser | Glu | Thr | Arg | Gln | Thr | Trp | Ala | Glu | Trp | Ala | Ala | Ala | His | Trp | Trp |
| | | | 435 | | | | | 440 | | | | | 445 | | |
| Gln | Leu | Thr | Leu | Gly | Ala | Thr | Cys | Ala | Leu | Pro | Leu | Ala | Gly | Leu | Leu |
| | | 450 | | | | | 455 | | | | | 460 | | | |
| Ala | Cys | Cys | Ala | Lys | Cys | Leu | Tyr | Tyr | Leu | Arg | Gly | Ala | Ile | Ala | Pro |
| 465 | | | | | 470 | | | | | 475 | | | | | 480 |

Arg (2) INFORMATION FOR SEQ ID NO:2:

(i) SEQUENCE CHARACTERISTICS:
        (A) LENGTH: 263 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: E2 glycoprotein (ix) FEATURE:
        (A) NAME/KEY: Protein
        (B) LOCATION: 1..263
        (D) OTHER INFORMATION: /note="E2 glycoprotein"

(xi) SEQUENCE DESCRIPTION: SEQ ID NO:2:

```
Ala Gly Leu Gln Pro Arg Ala Asp Met Ala Ala Pro Pro Thr Leu Pro
 1               5                  10                  15
Gln Pro Pro Arg Ala His Gly Gln His Tyr G (B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

```
Thr Leu Pro Gln Pro Pro Arg Ala His Gly Gln His His Tyr Gly His
1               5                   10                  15
His His His Gln Leu
        20
```

(2) INFORMATION FOR SEQ ID NO:4:

(i) SEQUENCE CHARACTERISTICS:
    (A) LENGTH: 27 amino acids
    (B) TYPE: amino acid
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

```
Ala Pro Pro Thr Leu Pro Gln Pro Pro Arg Ala His Gly Gln His Tyr
1               5                   10                  15
Gly His His His His Gln Leu Pro Phe Leu Gly
            20                  25
```

(2) INFORMATION FOR SEQ ID NO:5:

(i) SEQUENCE CHARACTERISTICS:
    (A) LENGTH: 28 amino acids
    (B) TYPE: amino acid
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

```
Ala Pro Pro Met Pro Pro Gln Pro Pro Arg Ala His Gly Gln His His
1               5                   10                  15
Tyr Gly His His His His Gln Leu Pro Phe Leu Gly
            20                  25
```

(2) INFORMATION FOR SEQ ID NO:6:

(i) SEQUENCE CHARACTERISTICS:
    (A) LENGTH: 27 amino acids
    (B) TYPE: amino acid
    (D) TOPOLOGY: linear (ii) MOLECULE TYPE: peptide (iii) HYPOTHETICAL: NO (iv) ANTI-SENSE: NO (v) FRAGMENT TYPE: internal ( x i ) SEQUENCE DESCRIPTION: SEQ ID NO:6:

Asn Gln Gln Ser Arg Trp Gly Leu Gly Ser Pro Asn Cys His Gly Pro
1               5                   10                  15

Asp Trp Ala Ser Pro Val Cys Gln Arg His Ser
            20                  25

( 2 ) INFORMATION FOR SEQ ID NO:7:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

Asn Gln Gln Ser Arg Trp Gly Leu Gly Ser Pro Asn Cys His Gly Pro
1               5                   10                  15

Asp Trp Ala Ser Pro Val Cys Gln Arg His Ser
            20                  25

What is claimed is:

1. A peptide having the formula:

a—Y—b, wherein:
Y is a sequence of at least six amino acids taken as a block from the amino acid sequence of the E2 glycoprotein of a strain of rubella virus that corresponds to $AA_{11}$–$AA_{37}$ of the E2 glycoprotein of the therein strain of rubella virus, in which block the sequence extends in the N terminus to C terminus direction of the native amino acid sequence,
a is selected from the group consisting of:
  (i) an amino terminus;
  (ii) a sequence of one to eight amino acids;
  (iii) a substituent effective to facilitate coupling; and
  (iv) a substituent effective to improve the immunogenic or antigenic activity of the peptide; and
b is selected from the group consisting of:
  (i) a carboxy terminus;
  (ii) a sequence of one to eight amino acids;
  (iii) a substituent effective to facilitate coupling; and
  (iv) a substituent effective to improve the immunogenic or antigenic activity of the peptide.

2. The peptide according to claim 1, wherein said strain of rubella is the Therien strain.

3. The peptide according to claim 2, comprising BCH-463 (Seq. ID No: 3).

4. The peptide according to claim 2, comprising BCH-481 (Seq. ID No: 4).

5. The peptide according to claim 1, wherein said strain is RA 27/3.

6. The peptide according to claim 5, comprising BCH-933 (Seq. ID No: 5).

7. A mixture or combination comprising at least two different peptides according to claim 1.

8. A mixture or combination comprising:
  (i) at least one peptide according to claim 1; and
  (ii) at least one of any other antigen of the rubella virus.

9. The mixture or combination according to claim 8, wherein said peptide of part (i) is selected from the group consisting of: BCH-463 (Seq. ID No: 3), BCH-481 (Seq. ID No: 4), BCH-933 (Seq. ID No: 5).

10. The mixture or combination according to claim 9, wherein said peptide of part (i) is BCH-481 (Seq. ID No: 4).

11. The mixture or combination according to claim 8, wherein said peptide of part (ii) is a peptide of the E1 protein of the following formula:

a—X—b wherein:
X is a sequence of at least six amino acids taken as a block from the amino acid sequence of the E1 glycoprotein of a strain of rubella virus that corresponds to $AA_{213}$–$AA_{239}$ of the E1 glycoprotein of the Therien strain of rubella virus, which block maintains the sequence and N terminus to C terminus direction of the native amino acid sequence; and
a and b are as defined in claim 1.

12. The mixture or combination according to claim 11, wherein at least one of said peptide of E1 glycoprotein is peptide BCH-178 (Seq. ID No: 7) cyclic.

13. The mixture or combination according to claim 12, wherein said peptide of part (i) is BCH-481 (Seq. ID No: 4), and said peptide of part (ii) is BCH-178 (Seq. ID No: 7) cyclic.

14. The mixture or combination according to claim 12, wherein the peptide of part (i) is a mixture of BCH-481 (Seq. ID No: 4) and BCH-933 (Seq. ID No: 5), and the peptide of part (ii) is BCH-178 (Seq. ID No: 7).

* * * * *

UNITED STATES PATENT AND TRADEMARK OFFICE
CERTIFICATE OF CORRECTION

PATENT NO. : 5,427,792
DATED : June 27, 1995
INVENTOR(S) : M. ZREIN et al

It is certified that error appears in the above-identified patent and that said Letters Patent is hereby corrected as shown below:

Column 25, line 40, delete "therein" and replace by --Therien --.

Signed and Sealed this

Nineteenth Day of December, 2000

Attest:

Q. TODD DICKINSON

*Attesting Officer*     *Commissioner of Patents and Trademarks*